United States Patent
Baloglu

(10) Patent No.: US 12,318,386 B2
(45) Date of Patent: Jun. 3, 2025

(54) COMBINATION OF XPO1 INHIBITORS AND SECOND AGENTS FOR THE TREATMENT OF PROSTATE CANCER

(71) Applicant: Karyopharm Therapeutics Inc., Newton, MA (US)

(72) Inventor: Erkan Baloglu, Stoneham, MA (US)

(73) Assignee: Karyopharm Therapeutics Inc., Newton, MA (US)

( * ) Notice: Subject to any disclaimer, the term of this patent is extended or adjusted under 35 U.S.C. 154(b) by 994 days.

(21) Appl. No.: 17/273,884

(22) PCT Filed: Sep. 5, 2019

(86) PCT No.: PCT/US2019/049689
§ 371 (c)(1),
(2) Date: Mar. 5, 2021

(87) PCT Pub. No.: WO2020/051294
PCT Pub. Date: Mar. 12, 2020

(65) Prior Publication Data
US 2021/0315897 A1    Oct. 14, 2021

Related U.S. Application Data

(60) Provisional application No. 62/803,136, filed on Feb. 8, 2019, provisional application No. 62/728,267, filed on Sep. 7, 2018.

(51) Int. Cl.
| | |
|---|---|
| *A61K 31/506* | (2006.01) |
| *A61K 9/00* | (2006.01) |
| *A61K 31/433* | (2006.01) |
| *A61K 31/573* | (2006.01) |
| *A61K 31/58* | (2006.01) |
| *A61P 35/00* | (2006.01) |

(52) U.S. Cl.
CPC .......... *A61K 31/506* (2013.01); *A61K 9/0053* (2013.01); *A61K 31/433* (2013.01);
(Continued)

(58) Field of Classification Search
CPC .................................................. A61K 31/506
See application file for complete search history.

(56) References Cited

U.S. PATENT DOCUMENTS

9,738,624 B2 * 8/2017 Baloglu ................. A61P 35/00
10,407,405 B2 * 9/2019 Baloglu .................. A61P 3/04
(Continued)

FOREIGN PATENT DOCUMENTS

| WO | WO-2015/065919 A1 | 5/2015 |
| WO | WO-2020/051294 A1 | 3/2020 |

OTHER PUBLICATIONS

Wei et al. The Oncologist 2018, 23, 656-e64 (Year: 2018).*
(Continued)

*Primary Examiner* — Matthew P Coughlin
(74) *Attorney, Agent, or Firm* — Foley Hoag LLP

(57) ABSTRACT

This invention relates to a method of treating prostate cancer comprising administering a compound of Formula (I) or a salt thereof in combination with either abiraterone or enzalutamide.

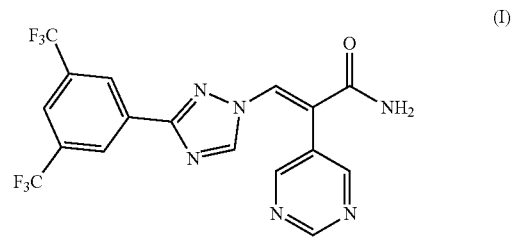

(I)

8 Claims, 7 Drawing Sheets

(52) U.S. Cl.
CPC ............ *A61K 31/573* (2013.01); *A61K 31/58* (2013.01); *A61P 35/00* (2018.01)

(56) References Cited

U.S. PATENT DOCUMENTS

| | | | |
|---|---|---|---|
| 11,124,493 B2* | 9/2021 | Baloglu | .................. A61P 37/06 |
| 2016/0152596 A1* | 6/2016 | Baloglu | ............... C07D 405/06 514/378 |

OTHER PUBLICATIONS

Ryan et al. Lancet Oncol. 2015, 16, 152-160 (Year: 2015).*

Aboukameel et al., "Down-regulation of AR splice variants through XPO1 suppression contributes to the inhibition of prostate cancer progression," Oncotarget, 9(82):35327-35342 (2018).

Argueta et al., "Disruption of nuclear export with selinexor or KPT-8602 reduces androgen receptor expression and leads to potent anti-tumor activity in preclinical models of androgen-independent prostate cancer," Cancer Research, 77(13):1538-7445 (2017).

International Search Report and Written Opinion for International Application No. PCT/US2019/049689 dated Jan. 13, 2020.

Irfana et al., "Down-regulation of AR splice variants through XPO1 suppression contributes to the inhibition of prostate cancer progression," Cancer Research, 78(13):2492 (2018).

Xiao et al., "A phase II trial of slinexor, an oral selective inhibitor of nuclear export compound, in abiraterone- and/or enxalutamide-refractory metastatic castration-resistant prostate cancer," The Oncologist, 23(6):656-e64 (2018).

Zhang et al., "Eltanexor (KPT-8602), a secondgeneration selective inhibitor of nuclear export (SINE) compound, in patients with metastatic castration-resistant prostate cancer (mCRPC)," Journal of Clinical Oncology, 37:1-3 (2019).

* cited by examiner

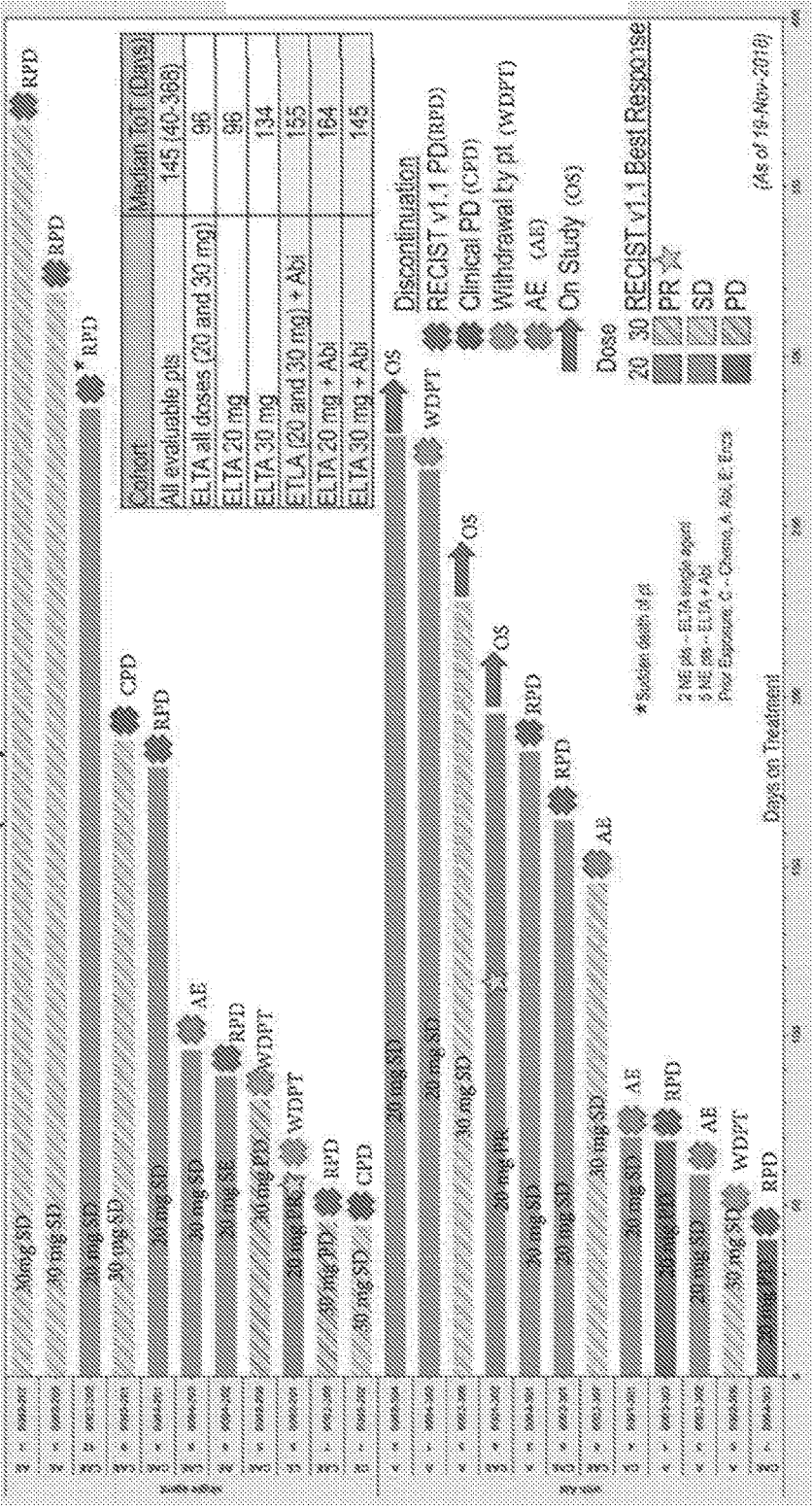

COMBINATION OF XPO1 INHIBITORS AND SECOND AGENTS FOR THE TREATMENT OF PROSTATE CANCER

RELATED APPLICATION(S)

This application is the U.S. National Stage of International Application No. PCT/US2019/049689, filed on Sep. 5, 2019, which designates the U.S., published in English, and claims the benefit of U.S. Provisional Application Nos. 62/728,267, filed on Sep. 7, 2018 and 62/803,136, filed on Feb. 8, 2019. The entire teachings of the above applications are incorporated herein by reference.

BACKGROUND OF THE INVENTION

Among men in the United States, prostate cancer is the most common malignancy and the second leading cause of mortality behind lung cancer. Since the discovery of the androgen dependence of prostate cancer in 1941 by Huggins and colleagues, androgen deprivation therapy (ADT) has remained the mainstay of treatment for prostate cancer. A better understanding of the androgen receptor (AR) signaling pathway and mechanisms of resistance to castration over the past decade has led to the discovery of novel AR targeting agents (i.e., anti-androgen therapies). The two main classes of anti-androgen therapy are androgen biosynthesis inhibitors (e.g., abiraterone) and androgen receptor blockers (e.g., enzalutamide). Although these anti-androgen agents are useful in the treatment of prostate cancer, in particular castration-resistant prostate cancer (CRPC), patients tend to develop resistance. One of the key mechanisms involved in resistance to abiraterone and enzalutamide is the expression of constitutively activated AR splice variant that are refractory to anti-androgen agents. The anti-AR treatment-induced AR splice variants activate cell cycle genes such as UBE2C without requiring the presence of full length AR, leading to prostate cancer survival and progression in castrate condition. As such, there is a need for improvements in the treatment of prostate cancer.

SUMMARY OF THE INVENTION

This invention relates to a method of treating prostate cancer comprising administering a compound of Formula (I) or a salt thereof in combination with either abiraterone or enzalutamide.

One embodiment is a method of treating prostate cancer in an abiraterone-refractory subject in need thereof. The method comprises administering to the subject a combination of a first amount of abiraterone, and a second amount of a compound represented by Formula (I)

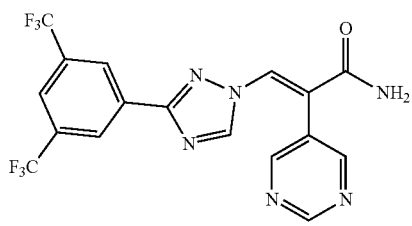

or a pharmaceutically acceptable salt thereof, wherein the first and second amounts together comprise an effective amount.

Another embodiment is a method of treating prostate cancer in an enzalutamide-refractory subject in need thereof. The method comprises administering to the subject a combination of a first amount of enzalutamide, and a second amount of a compound represented by Formula (I)

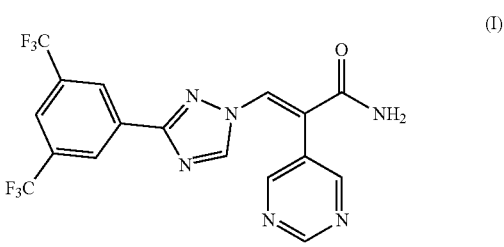 [SMILES: NC(=O)/C(=C/n1cnc(-c2cc(C(F)(F)F)cc(C(F)(F)F)c2)n1)c1cncnc1]

or a pharmaceutically acceptable salt thereof, wherein the first and second amounts together comprise an effective amount.

Yet another embodiment is a method of treating prostate cancer in an enzalutamide -naïve subject in need thereof. The method comprises administering to the subject a combination of a first amount of a compound represented by Formula (I)

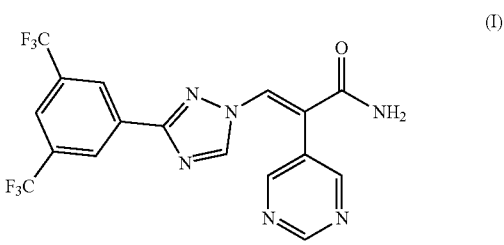 [SMILES: NC(=O)/C(=C/n1cnc(-c2cc(C(F)(F)F)cc(C(F)(F)F)c2)n1)c1cncnc1]

or a pharmaceutically acceptable salt thereof, and a second amount of enzalutamide, wherein the first and second amounts together comprise an effective amount.

In another embodiment is a method of treating prostate cancer in an abiraterone-naïve subject in need thereof. The method comprises administering to the subject a combination of a first amount of a compound represented by Formula (I)

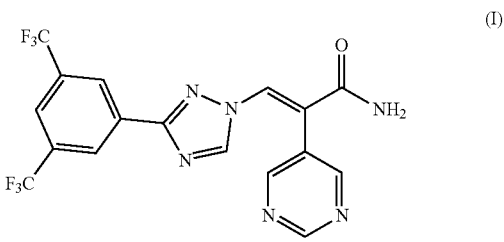 [SMILES: NC(=O)/C(=C/n1cnc(-c2cc(C(F)(F)F)cc(C(F)(F)F)c2)n1)c1cncnc1]

or a pharmaceutically acceptable salt thereof, and a second amount of abiraterone, wherein the first and second amounts together comprise an effective amount.

A further embodiment is a method of treating prostate cancer in an abiraterone-refractory subject in need thereof, comprising the combination administration to the subject over a 28-day treatment cycle of a first amount of abiraterone, and a second amount of a compound represented by Formula (I)

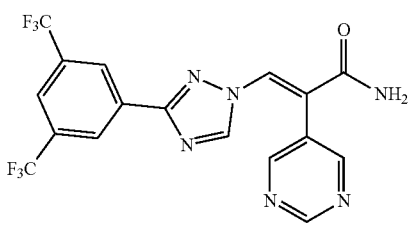

(I)

or a pharmaceutically acceptable salt thereof, wherein the first and second amounts together comprise an effective amount; and wherein the compound of Formula (I) is administered on days 1-5, 8-12, 15-19, and 22-26 of the 28-day treatment cycle and abiraterone is administered daily during the 28-day treatment cycle.

Another embodiment is a method of treating prostate cancer in an enzalutamide-refractory subject in need thereof, comprising the combination administration to the subject over a 28-day treatment cycle of a first amount of enzalutamide, and a second amount of a compound represented by Formula (I)

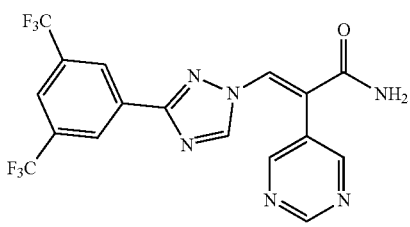

(I)

or a pharmaceutically acceptable salt thereof, wherein the first and second amounts together comprise an effective amount; and wherein the compound of Formula (I) is administered on days 1-5, 8-12, 15-19, and 22-26 of the 28-day treatment cycle and enzalutimde is administered daily during the 28-day treatment cycle.

Yet another embodiment is a method of treating prostate cancer in an enzalutamide -naïve subject in need thereof, comprising the combination administration to the subject over a 28-day treatment cycle of a first amount of a compound represented by Formula (I)

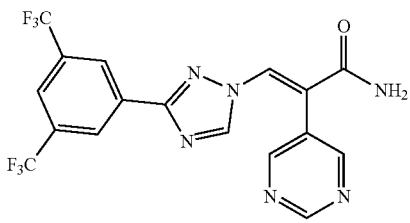

(I)

or a pharmaceutically acceptable salt thereof, and a second amount of enzalutamide, wherein the first and second amounts together comprise an effective amount; and wherein the compound of Formula (I) is administered on days 1-5, 8-12, 15-19, and 22-26 of the 28-day treatment cycle and enzalutamide is administered daily during the 28-day treatment cycle.

A further embodiment is a method of treating prostate cancer in an abiraterone-naïve subject in need thereof, comprising the combination administration to the subject over a 28-day treatment cycle of a first amount of a compound represented by Formula (I)

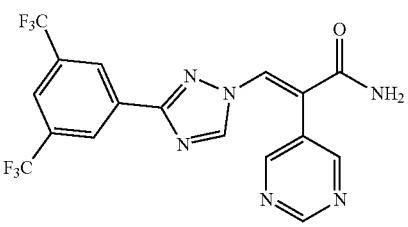

(I)

or a pharmaceutically acceptable salt thereof, and a second amount of abiraterone; and wherein the compound of Formula (I) is administered on days 1-5, 8-12, 15-19, and 22-26 of the 28-day treatment cycle and abiraterone is administered daily during the 28-day treatment cycle.

Yet another embodiment is the use of a pharmaceutical composition comprising a first amount of a compound represented by Formula (I) or a pharmaceutically acceptable salt and a second amount of either abiraterone or enzalutamide for the manufacture of a medicament for use in treating prostate cancer.

Another embodiment, a pharmaceutical composition comprising a first amount of a compound represented by Formula (I) or a pharmaceutically acceptable salt and a second amount of either abiraterone or enzalutamide for use in treating prostate cancer.

Yet another embodiment is the use of a first amount of a compound represented by Formula (I) or a pharmaceutically acceptable salt and a second amount of either abiraterone or enzalutamide for the manufacture of a medicament for use in treating prostate cancer, wherein the prostate cancer is in a subject as described herein (e.g., abiraterione refractory or naïve or enzalutamide refractor or naïve).

Yet another embodiment is the use of a first amount of a compound represented by Formula (I) or a pharmaceutically acceptable salt and a second amount of either abiraterone or enzalutamide for use in treating prostate cancer, wherein the prostate cancer is in a subject as described herein (e.g., abiraterione refractory or naïve or enzalutamide refractor or naïve).

BRIEF DESCRIPTION OF THE DRAWINGS

FIG. 8 is a plot showing Time on Treatment (ToT) for evaluable patients.

DETAILED DESCRIPTION OF THE INVENTION

Figure 1:
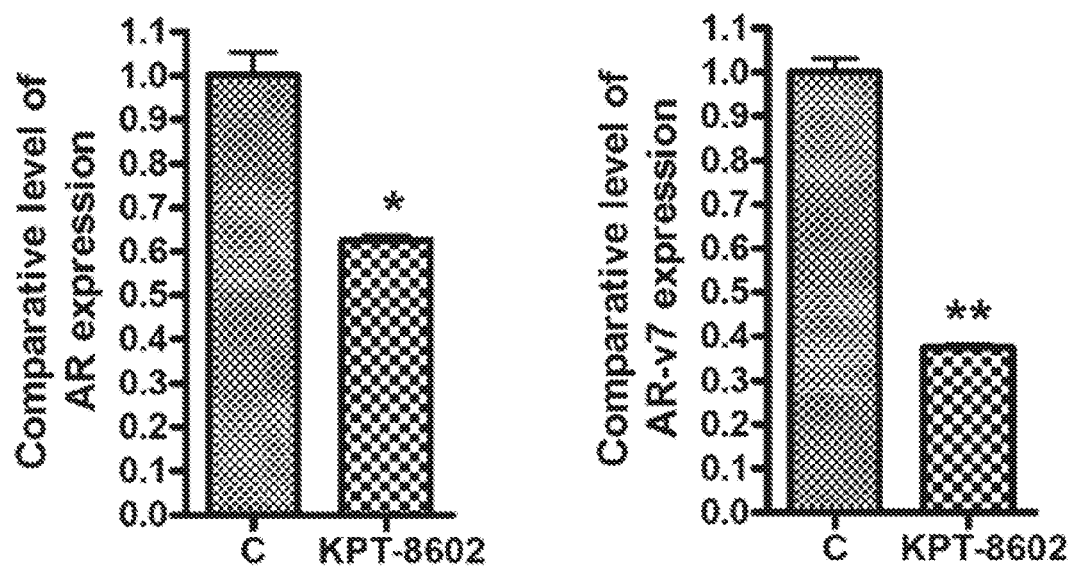
FIG. 1 are graphs showing the levels of AR or AR-v7 mRNA levels in 22Rv1 prostate cancer cells before and after exposure to KPT-8602.

A description of example embodiments of the invention follows.

The compound represented by Formula I

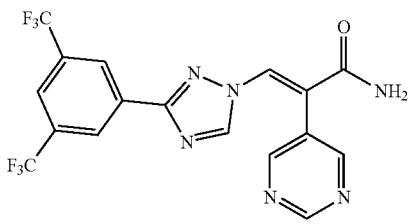

(including salts thereof) is commonly referred to as KPT-8602 or eltanexor. The compound represented by Formula I is an inhibitor of nuclear export currently in Phase ½ clinical trial in patients with relapsed/refractory multiple myeloma. Eltanexor blocks the key nuclear export protein XPO1 to force nuclear retention of tumor suppressor proteins (TSPs). As Eltanexor acts through induction of TSPs, it is selectively cytotoxic for cells with genomic damage, i.e., for tumor cells, both in vitro and in vivo.

Abiraterone acetate is an FDA approved anti-androgen for the treatment of prostate cancer sold under the brand name Zytiga ([(3S,8R,9S,10R,13S,14S)-10,13-dimethyl-17-pyridin-3-yl-2,3,4,7,8,9,11,12,14,15-decahydro-1H-cyclopenta[a]phenanthren-3-yl]acetate) and represented by the following structural formula:

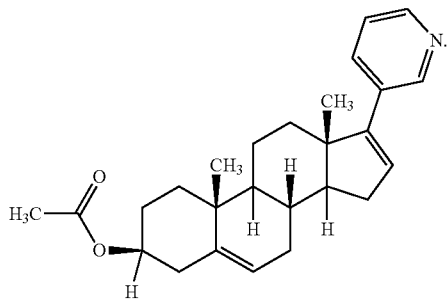

Abiraterone acetate works as an androgen biosynthesis inhibitor. Specifically, abiraterone acetate is a highly selective CYP17 inhibitor that causes a decrease in adrenal androgens, thus indirectly inhibiting the AR signaling pathway. As used herein, "abiraterone" includes the acetate salt of [(3S,8R,9S,10R,13S,14S)-10,13-dimethyl-17-pyridin-3-yl-2,3,4,7,8,9,11,12,14,15-decahydro-1H-cyclopenta[a]phenanthren-3-yl] as sold under the brand name Zytiga as well the free-hydroxy compound represented by the following structural formula

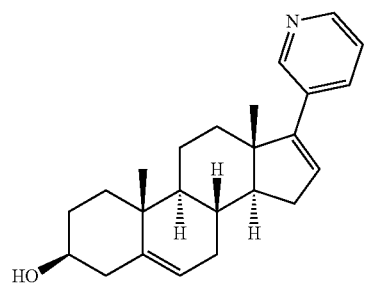

and any other esterified forms of the free-hydroxy compound.

Enzalutamide is an FDA approved AR blocker. Enzalutamide binds with high affinity to the ligand-binding domain of the AR. It prevents nuclear translocation of the AR, DNA binding, and co-activator recruitment of the ligand-receptor complex. Enzalutamide is available under the brand name Xtandi (4-{3-[4-cyano-3-(trifluoromethyl)phenyl]-5,5-dimethyl-4-oxo-2-sulfanylideneimidazolidin-1-yl}-2-fluoro-N-methylbenzamide) and is represented by the following structural formula:

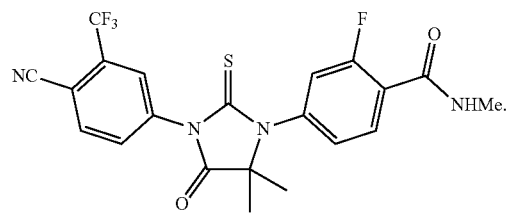 [SMILES: CNC(=O)c1ccc(N2C(=S)N(c3ccc(C#N)c(C(F)(F)F)c3)C(=O)C2(C)C)cc1F]

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Examples of non-toxic organic or inorganic base addition salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection criteria for the appropriate salt will be known to one skilled in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

As used herein, "subject" refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

As used herein, a subject is "enzalutamide-refractory" when the subject has developed resistance to the therapeutic effects of enzalutamide. Resistance can be partial or complete and can be determined by a clinician monitoring the progress of the suject's prostate cancer.

As used herein, a subject is "enzalutamide naïve" when the subject has not previously received enzalutamide as a therapy.

As used herein, a subject is "abiraterone-refractory" when the subject has developed resistance to the therapeutic effects of abiraterone. Resistance can be partial or complete and can determined by a clinician monitoring the progress of the subject's prostate cancer.

As used herein, a subject is "abiraterone naïve" when the subject has not previously received abiraterone as a therapy.

As used herein, "prostate cancer" includes primary prostate cancer (e.g., acinar adenocarcinoma), castration resistant prostate cancer (CRPC) and metastatic castration resistant prostate cancer (mCRPC).

In a first embodiment, the invention relates to a method of treating prostate cancer in an abiraterone-refractory subject in need thereof, comprising the combination administration to the subject of a first amount of abiraterone, and a second amount of a compound represented by Formula (I):

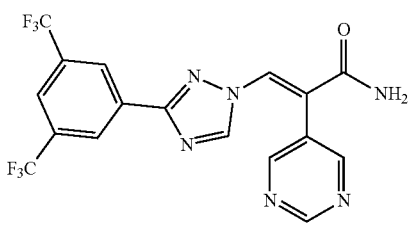

or a pharmaceutically acceptable salt thereof, wherein the first and second amounts together comprise an effective amount.

In a second embodiment, the invention relates to a method of treating prostate cancer in an enzalutamide-refractory subject in need thereof, comprising the combination administration to the subject of a first amount of enzalutamide, and a second amount of a compound represented by Formula (I):

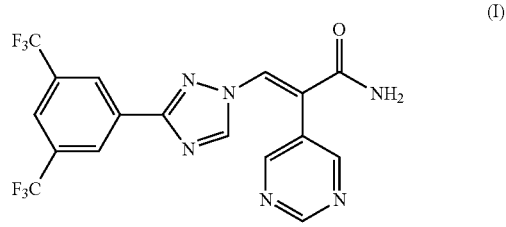 [SMILES: NC(=O)/C(=C/n1cnc(-c2cc(C(F)(F)F)cc(C(F)(F)F)c2)n1)c1cncnc1]

or a pharmaceutically acceptable salt thereof, wherein the first and second amounts together comprise an effective amount.

In a third embodiment, the invention relates to a method of treating prostate cancer in an enzalutamide-naïve subject in need thereof, comprising the combination administration to the subject of a first amount of a compound represented by Formula (I):

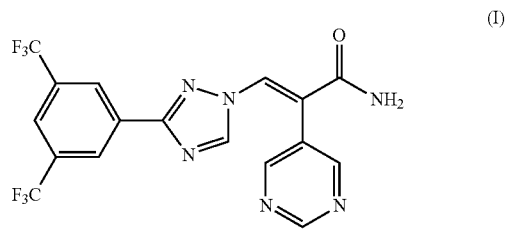 [SMILES: NC(=O)/C(=C/n1cnc(-c2cc(C(F)(F)F)cc(C(F)(F)F)c2)n1)c1cncnc1]

or a pharmaceutically acceptable salt thereof, and a second amount of enzalutamide, wherein the first and second amounts together comprise an effective amount.

effective amount.

In a fourth embodiment, the invention relates to a method of treating prostate cancer in an abiraterone-naïve subject in need thereof, comprising the combination administration to the subject of a first amount of a compound represented by Formula (I):

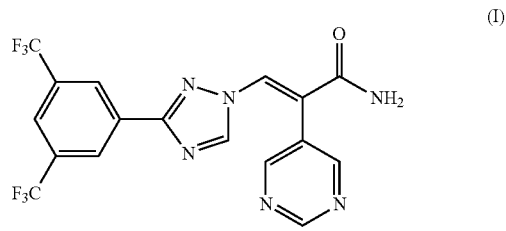 [SMILES: NC(=O)/C(=C/n1cnc(-c2cc(C(F)(F)F)cc(C(F)(F)F)c2)n1)c1cncnc1]

or a pharmaceutically acceptable salt thereof, and a second amount of abiraterone, wherein the first and second amounts together comprise an effective amount.

In a fifth embodiment, the invention relates to a method of treating prostate cancer in an abiraterone-refractory subject in need thereof, comprising the combination administration to the subject over a 28-day treatment cycle of a first amount of abiraterone, and a second amount of a compound of Formula (I):

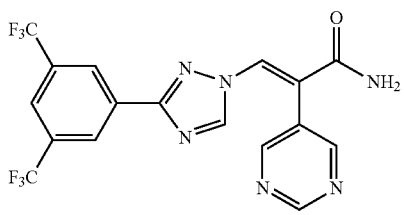

(I)

or a pharmaceutically acceptable salt thereof, wherein the first and second amounts together comprise an effective amount; and wherein the compound of Formula (I) is administered on days 1-5, 8-12, 15-19, and 22-26 of the 28-day treatment cycle and abiraterone is administered daily during the 28-day treatment cycle.

In a sixth embodiment, the invention relates to a method of treating prostate cancer in an enzalutamide-refractory subject in need thereof, comprising the combination administration to the subject over a 28-day treatment cycle of a first amount of enzalutamide, and a second amount of a compound of Formula (I):

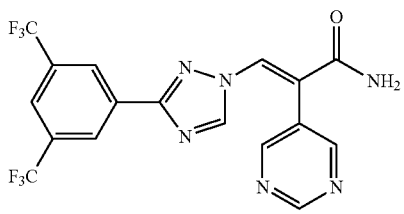

(I)

or a pharmaceutically acceptable salt thereof, wherein the first and second amounts together comprise an effective amount; and wherein the compound of Formula (I) is administered on days 1-5, 8-12, 15-19, and 22-26 of the 28-day treatment cycle and enzalutimde is administered daily during the 28-day treatment cycle.

In a seventh embodiment, the invention relates to a method of treating prostate cancer in an enzalutamide-naïve subject in need thereof, comprising the combination administration to the subject over a 28-day treatment cycle of a first amount of a compound of Formula (I):

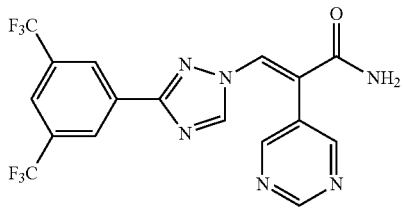

(I)

or a pharmaceutically acceptable salt thereof, and a second amount of enzalutamide, wherein the first and second amounts together comprise an effective amount; and wherein the compound of Formula (I) is administered on days 1-5, 8-12, 15-19, and 22-26 of the 28-day treatment cycle and enzalutamide is administered daily during the 28-day treatment cycle.

In an eighth embodiment, the invention relates to a method of treating prostate cancer in an abiraterone-naïve subject in need thereof, comprising the combination administration to the subject over a 28-day treatment cycle of a first amount of a compound of Formula (I):

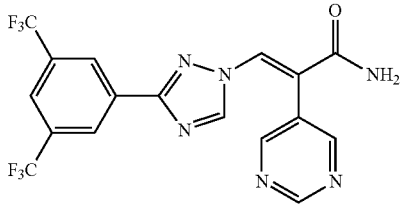

(I)

or a pharmaceutically acceptable salt thereof, and a second amount of abiraterone; and wherein the compound of Formula (I) is administered on days 1-5, 8-12, 15-19, and 22-26 of the 28-day treatment cycle and abiraterone is administered daily during the 28-day treatment cycle.

In a first aspect of the invention, in any one of embodiments one, two, three, four, five, six, seven or eight, the subject has received one previous treatment regimen of docetaxel for prostate cancer treatment.

In a second aspect of the invention, in any one of embodiments one, two, three, four, five, six, seven or eight, the subject has previously received at least three treatment regimens for prostate cancer; wherein each treatment regimen comprised administering to the subject a different active ingredient.

In a third aspect of the invention, in any one of embodiments one, two, three, four, five, six, seven or eight, the subject has previously received at least two treatment regimens for prostate cancer; wherein each treatment regimen comprised administering to the subject a different active ingredient.

In a fourth aspect of the invention, in any one of embodiments one, two, three, four, five, six, seven or eight, the subject has previously received at least one treatment regimen for prostate cancer; and if the subject previously received more than one treatment regimen, each treatment regimen comprised administering to the subject a different active ingredient.

In a fifth aspect of the invention, in any one of embodiments one, four, five or eight, or in any one of the first, second, third or fourth aspects thereof the abiraterone is abiraterone acetate.

In a sixth aspect of the invention, in any one of embodiments one, four, five or eight or in any one of the first, second, third, fourth or fifth aspects thereof the abiraterone is administered orally once daily at a dose of from about 200 mg to about 2000 mg. For example, in a specific aspect the abiraterone is administered orally once daily at a dose of about 500 mg to about 1000 mg. In another specific aspect, abiraterone is administered orally once daily at a dose of 1000 mg. In yet another specific aspect, abiraterone is administered orally once daily at a dose of 750 mg. In a further specific aspect, abiraterone is administered orally once daily at a dose of 500 mg.

In a seventh aspect of the invention, in any one of embodiments one, four, five or eight, or in any one of aspects or any specific aspects thereof prednisone is administered in combination with abiraterone. In a specific aspect, prednisone is administered orally at a dose of from about 1 mg to about 20 mg. In another specific aspect, prednisone is administered orally at a dose of about 5 mg to about 15 mg. In yet another specific aspect, prednisone is administered orally at a dose of 10 mg. In yet a further specific aspect, prednisone is administered orally twice daily at a dose of 5 mg each time.

In an eighth aspect of the invention, in any one of embodiments two or three, six or seven, or in any aspects or any specific aspects thereof, enzalutamide is administered orally once daily at a dose of about 40 to about 320 mg. In a specific embodiment, enzalutamide is administered orally once daily at a dose of about 80 mg to about 240 mg. In yet another specific embodiment, enzalutamide is administered orally once daily at a dose of about 120 mg to about 160 mg. In yet a further specific aspect, enzalutamide is administered orally once daily at a dose of 160 mg.

In a ninth aspect of the invention, in any one of embodiments one, two, three, four, five, six, seven or eight or any aspects or specific aspects thereof, the compound of Formula (I) is administered at a dose of about 5 mg to about 40 mg per day. In a specific aspect, the compound of Formula (I) is administered at a dose of about 10 mg to about 30 mg per day. In a further specific aspect, the compound of Formula (I) is administered at a dose of 20 mg per day.

In a tenth aspect of the invention, in any one of embodiment five, six, seven or eight or any aspects or specific aspects thereof, the cycle is repeated at least two times. In a specific aspect, the cycles are consecutive.

In a eleventh aspect of the invention, in any one of embodiment five, six, seven or eight or any aspects or specific aspects thereof, the cycle is repeated at least three times. In a specific aspect, the cycles are consecutive.

In a twelfth aspect of the invention, in any one of embodiment five, six, seven or eight or any aspects or specific aspects thereof, the cycle is repeated at least two times.

In a thirteenth aspect of the invention, in any one of embodiments one, two, three, four, five, six, seven or eight, or any aspects or specific aspects thereon the prostate cancer is metastatic castration-resistant prostate cancer or castration-resistant prostate cancer.

In a fourteenth aspect of the invention, in any one of embodiments one, four, five or eight the subject is enzalutamide naïve.

In a fifteenth aspect of the invention, in any one of embodiments one, four, five or eight the subject is enzalutamide refractory.

In a sixteenth aspect of the invention, in any one of embodiments two, three, six or seven the subject is abiraterone naïve.

In a seventeenth aspect of the invention, in any one of embodiments two, three, six or seven the subject is abiraterone refractory.

In a ninth embodiment, the invention relates to a kit for treating prostate cancer. The kit comprises the compound of Formula (I) or a pharmaceutically acceptable salt thereof and instructions for use with the anti-androgen therapeutic (e.g., abiraterone or enzalutamide) according to the method of the invention and optionally a device for administering the compounds of the kit. In a particular aspect, both the compound of Formula (I) and the anti-androgen therapeutic are present in the kit in an effective amount. In another particular aspect, the at least one of the compound of Formula (I) or the anti-androgen therapeutic is present in the kit in a sub-therapeutic dose.

Combination Therapy/Coadministration/Combined Administration

In certain embodiments, the combined administration of the compound of Formula (I) and the anti-androgen therapeutic (e.g, abiraterone or enzalutamide) can provide an enhanced therapeutic effect or can demonstrate synergy (i.e. show a therapeutic effect that is greater than the additive effect resulting from separate administration of each component of the combination). An advantage of a synergistic effect of the combination therapy is the ability to use less of each agent than is needed when each is administered alone. As such, undesirable side effects associated with the agents are reduced (partially or completely). The presence of synergistic effects can be determined using suitable method for assessing drug interaction. Suitable methods include, for example, the Sigmoid-Emax equation, the equation of Loewe additivity and the median-effect equation. The corresponding graphs associated with the equations referred to above are the concentration-effect curve, isobologram curve and combination index curve, respectively.

As used herein, "an enhanced therapeutic effect" includes an improved therapeutic profile. Examples of enhanced therapeutic effects include the ability to use a less of one or both agents administered in the combination therapy than is needed when each is used alone, a prolonged therapeutic window of one or both compounds of the combination therapy, reduced side effects following administration of the combination therapy, reduced resistance of prostate cancer cells to one or both compounds of the combination (e.g, reduced resistance of the prostate cancer to either abiraterone or enzalutamide) and sensitization of target cells to the action of one or both compounds of the combination therapy (e.g, increased sensitivity of prostate cancer cells to anti-androgen therapy, such as enzalutamide or abiraterone).

As used herein, the combined administration (also referred to herein as co-administration) refers to administration of a first amount of the compound of Formula (I) or a pharmaceutically acceptable salt thereof and a second amount of the anti-androgen therapeutic (e.g, abiraterone or enzalutamide), wherein the first and second amounts together comprise an effective amount.

As used herein, an amount effective to treat a disorder, or an "effective amount" refers to an amount of the compound of Formula (I) and abiraterone or enzalutamide that together (e.g., in combination) is effective, upon single or multiple dose administration to a subject or a cell, in curing, alleviating, relieving or improving one or more symptoms of the target disorder (e.g., prostate cancer).

In one embodiment, the compound of Formula (I) and abiraterone or enzalutamide are each administered in a respective effective amount (i.e., each in an amount which would be therapeutically effective if administered alone). In another embodiment, the compound of Formula (I) and abiraterone or enzalutamide are each administered in an amount which alone does not provide a therapeutic effect (a sub-therapeutic dose). In yet another embodiment, the compound of Formula (I) can be administered in an effective amount, while abiraterone or enzalutamide is administered in a sub-therapeutic dose. In still another embodiment, abiraterone or enzalutamide can be administered in an effective amount, while the compound of Formula (I) is administered in a sub-therapeutic dose.

In some embodiments, the compound of Formula (I) is administered simultaneously with the anti-androgen therapeutic (e.g., enzalutamide or abiraterone). Simultaneous administration typically means that both compounds enter the patient at essentially the same time, such as in a single pharmaceutical composition, for example, capsule or tablet having a fixed ratio of first and second amounts, or in multiple, separate capsules or tablets for each. Co-administration also include use of each compound of the combination therapy in a sequential manner in either order. When co-administration involves the separate administration of the first amount of a compound of Formula (I) or a pharmaceutically acceptable salt thereof and the second amount of the anti-androgen therapeutic (e.g., enzalutamide or abiraterone) the first and second amounts are administered sufficiently close in time to have the desired therapeutic effect. For example, the period of time between each administration, which can result in the desired therapeutic effect, can range from minutes to hours and can be determined taking into account the properties of each compound such as potency, solubility, bioavailability, plasma half-life and kinetic profile. For example, the compound of Formula (I) and the anti-androgen therapeutic can be administered in any order within about 24 hours of each other, within about 16 hours of each other, within about 8 hours of each other, within about 4 hours of each other, within about 1 hour of each other, within about 30 minutes of each other, within about 15 minutes or each other or within about 5 minutes of each other.

In one example, wherein the compounds are in solution, simultaneous administration can be achieved by administering a solution containing the combination of compounds. In another example, simultaneous administration of separate solutions, one of which contains the compound of Formula (I) and the other of which contains the anti-androgen therapeutic (e.g., enzalutamide or abiraterone, can be employed. In one example wherein the compounds are in solid form, simultaneous administration can be achieved by administering a composition containing the combination of compounds. Alternatively, simultaneous administration can be achieved by simultaneous administration of separate solid dosage forms.

In some embodiments, prednisone is administered before, during, or after the administration of the compound of Formula (I) and the anti-androgen therapeutic as described herein.

As used herein, the term "treat" or "treatment" is defined as the application or administration of the combination therapy described herein (e.g., the compound of Formula (I), and an anti-androgen therapeutic, such as enzalutamide or abiraterone) to a subject suffering from the target disorder (prostate cancer) in order to cure, heal, alleviate, relieve, alter, remedy, ameliorate, improve, delay progression or affect the disorder or one or more symptoms of the disorder.

In a particular embodiment, subjects can be treated with KPT-8602 and abiraterone, wherein the treatment comprises orally administering KPT-8602 for 5 days per week (QDx5) at a dose levels of 20 mg and continue with the dose and schedule of abiraterone and corticosteroids that they were receiving at the time of enrollment. For example, a typical dose of ZYTIGA (abiraterone acetate) is 1000 mg orally once daily with prednisone 5 mg orally twice daily. A full cycle of treatment can be 28 days long. A representative cycle of KPT-8602 dosing can be oral administration 5 out of 7 consecutive days in a week for a 28-day cycle (e.g., Days 1-5, 8-12, 15-19 and 22-26 of each 28-day cycle).

In other embodiments, the subjects are administered KPT-8602 for 5 days per week (QDx5) at a dose levels of 20 mg plus abiraterone and continue with the dose of abiraterone and corticosteroids that they were receiving at the time of enrollment and have previously received enzalutamide (i.e., are post-enzalutamide).

In another particular embodiment, subjects can be treated with KPT-8602 and enzalutamide, wherein the treatment comprises orally administering KPT-8602 for 5 days per week (QDx5) at a dose levels of 20 mg and continue with the dose and schedule of enzalutamide and optionally corticosteroids that they were receiving at the time of enrollment. A full cycle of treatment can be 28 days long. A representative cycle of KPT-8602 dosing can be oral administration 5 out of 7 consecutive days in a week for a 28-day cycle (e.g., Days 1-5, 8-12, 15-19 and 22-26 of each 28-day cycle).

In other embodiments, the subjects are administered KPT-8602 for 5 days per week (QDx5) at a dose levels of 20 mg plus enzalutamide and continue with the dose of enzalutamide and optionally corticosteroids that they were receiving at the time of enrollment and have previously received abiraterone (i.e., are post-aberaterone).

In all embodiments and aspects described herein the patient's prostate cancer cells are test positive for the AR splice variant, AR-V7.

Modes of Administration

Compositions of the present invention can be administered orally, parenterally (including subcutaneous, intramuscular, intravenous and intradermal), by inhalation spray, topically, rectally, nasally, buccally, transdermally, sublingually, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

The compound of Formula (I) and the anti-androgen therapeutic can each be formulated separately, in separate formulations (selected independently), or can be formulated together in a single formulation. "Composition" and "pharmaceutical composition," used herein, include: compositions comprising the compound of Formula (I), or a pharmaceutically acceptable salt thereof and a pharmaceutically acceptable carrier; compositions comprising the anti-androgen therapeutics (e.g., abiraterone or enzalutamide) or a pharmaceutically acceptable salt thereof and a pharmaceutically acceptable carrier; and compositions comprising the compound of Formula (I), or a pharmaceutically acceptable salt thereof, and the anti-androgenic therapeutic (e.g, enzalutamide or abiraterone), or a pharmaceutically acceptable salt thereof and optionally a pharmaceutically acceptable carrier.

When the compounds are formulated separately (e.g., in a composition comprising the compound and a pharmaceutically acceptable carrier), the amount of the compound (e.g., the compound of Formula (I)) should be such that, when administered in combination with the other compound (e.g., the anti-androgen therapeutic) to treat prostate cancer, the amount is an "effective amount."

The compounds can also be formulated in a single dosage form (a "unit dosage form"). Thus, one embodiment is a pharmaceutical composition comprising a first amount of the compound of Formula (I), or a pharmaceutically acceptable salt thereof, and a second amount of an anti-androgen therapeutic (e.g., enzalutamide or abiraterone), or a pharmaceutically acceptable salt thereof, wherein the first and second amounts together comprise an effective amount. In certain embodiments, the pharmaceutical composition further comprises a pharmaceutically acceptable carrier. The term "unit dosage form" refers to physically discrete units suitable as unitary dosage for subjects undergoing treatment, with each unit containing a predetermined quantity of active material calculated to product eh desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same of different for each dose.

As used herein, "pharmaceutically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

The phrase "pharmaceutically acceptable carrier" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat, cyclodextrins such as α-, β-, and γ-cyclodextrin, or chemically modified derivatives such as hydroxyalkylcyclodextrins, including 2- and 3-hydroxypropyl-β-cyclodextrins and self-emulsifying drug delivery systems (SEDDS) such as d-α-tocopherol polyethylene glycol 1000 succinate.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

Compositions for oral administration may be designed to protect the active ingredient against degradation as it passes through the alimentary tract, for example, by an outer coating of the formulation on a tablet or capsule.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound in a pharmaceutical composition of the invention can also be in micro-encapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

In another embodiment, a pharmaceutical composition can be provided as an extended (or "delayed" or "sustained") release composition. This delayed-release composition comprises a compound in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active components suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intravenous administration.

In some embodiments, pharmaceutically acceptable compositions of this invention are formulated for topical administration.

The amount of the compounds that can be combined with the carrier materials to produce a composition in a single unit dosage form will vary depending upon the host treated, the particular mode of administration and the activity of the compound employed.

It should also be understood that a specific dosage and treatment regimen for any particular subject will depend upon a variety of factors, including the activity of the specific compound employed, the age, body weight, general health, sex, diet, time of administration, rate of excretion, drug combination, the judgment of the treating physician and the severity of the particular disease being treated.

The pharmaceutical compositions of this invention comprising the compound of Formula (I), the anti-androgen therapeutics (e.g. enzalutamide or abiraterone), or a combination of the compound of Formula (I) and the anti-androgen therapeutic (e.g., enzalutamide or abiraterone) are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some embodiments, abiraterone is administered orally once daily at a dose of about 200 mg to about 2000 mg. In some embodiments, abiraterone is administered orally once daily at a dose of about 500 mg to about 1000 mg. In some embodiments, abiraterone is administered orally once daily at a dose of about 1000 mg. In some embodiments, abiraterone is administered orally once daily at a dose of 750 mg. In some embodiments, abiraterone is administered orally once daily at a dose of 500 mg.

In some embodiments, prednisone is administered in combination with abiraterone. In some embodiments, prednisone is administered orally at a dose of about 1 mg to 20 mg. In some embodiments, prednisone is administered orally at a dose of about 5 mg to 15 mg. In some embodiments, prednisone is administered orally at a dose of about 10 mg. In some embodiments, prednisone is administered orally twice daily at a dose of about 5 mg each time.

In some embodiments, enzalutamide is administered orally once daily at a dose of about 40 to about 320 mg. In some embodiments, enzalutamide is administered orally once daily at a dose of about 80 mg to about 240 mg. In some embodiments, enzalutamide is administered orally once daily at a dose of about 120 mg to about 160 mg. In some embodiments, enzalutamide is administered orally once daily at a dose of about 160 mg.

In some embodiments, the compound of Formula (I) is administered at a dose of about 5 mg to about 100 mg per day. In some embodiments, compound of Formula (I) is administered at a dose of about 5 mg to about 40 mg per day. In some embodiments, compound of Formula (I) is administered at a dose of about 10 mg to about 30 mg per day. In some embodiments, the compound of Formula (I) is administered at a dose of about 20 mg.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a composition of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

EXEMPLIFICATION

Materials:

Prostate Cancer Cell Lines: 22Rv1 and VCaP cells were purchased form American Type Culture Collection (ATCC, Manassas, VA) and maintained in RPMI1640 (Invitrogen, Carlsbad, CA) supplemented with 10% fetal bovine serum (FBS), 100 U/mL penicillin and 100 ug/ml streptomycin in a 5% CO2 atmosphere at 37° C.

KPT-8602 (Karyopharm Therapeutics Inc., Newton, MA) was dissolved in DMSO to make a 1 mM stock solution.

Statistical Analysis was conducted by subjecting the data to a Student's t-test using GraphPad Prism software. P<0.05 was considered statistically significant.

Prostate cancer RECIST category are used herein as the de facto standard for assessment of response in prostate tumors in patients on clinical trials.

Example 1. KPT-8602 Significantly Inhibits AR and AR Splice Variant, AR-v7, Prostate Cancer Cells Prostate cancer cell line 22Rv1 was treated with KPT-8602 and the effect of the treatment on the expression of AR and AR splice variant AR-v7 was determined. 22Rv1 cells were treated with 200 nM KPT-8602 for 48 hours and the mRNA expression levels of AR and AR-v7 before (control) and after treatment were measured by real-time RT-qPCR using High Capacity cDNA Reverse Transcription Kit and SYBR Green Master Mixture from Applied Biosystems (Waltham, MA). KPT-8602 significantly inhibited the mRNA expression of AR and AR-v7 (FIG. 1).

Figure 2:
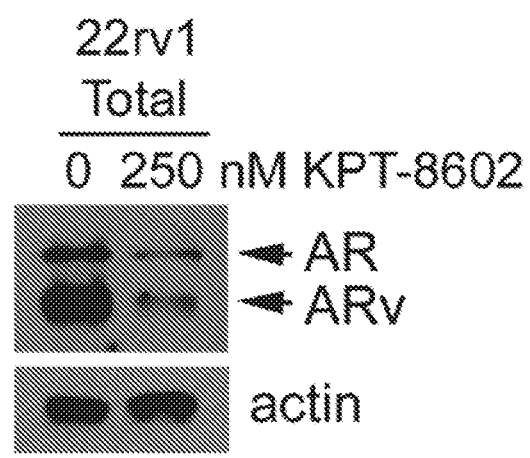
FIG. 2 is a Western blot analysis showing that KPT-8602 decreased protein levels of AR and ARv in 22Rv1 cells after treatment for 72 hours. *=p<0.05 and **=p<0.01.

Western blot analysis was also conducted on the 22Rv1 and VCaP cells before and after treatment (250 nM KPT-8602 for 72 hours) and total proteins were extracted from these cells and subjected to Western blot analysis to determine whether protein levels of AR and ARv were also decreased after the downregulation of AR and ARv mRNAs by KPT-8602. Western blot analysis showed that KPT-8602 significantly decreased protein levels of AR and ARv in 22Rv1 cells after treatment for 72 hours (FIG. 2).

Western Blot Analysis

Total proteins were subjected to 10 or 14% SDS-PAGE, and electrophoretically transferred to nitrocellulose membrane. The membranes were incubated with specific primary antibodies, and subsequently incubated with secondary antibody conjugated with peroxidase (Bio-rad, Hercules, CA). The signal was detected using the chemiluminescent detection system (PIERCE).

Example 2: Treatment of 22Rv1 Prostate Cancer Xenograft with KPT-8602

Figure 3:
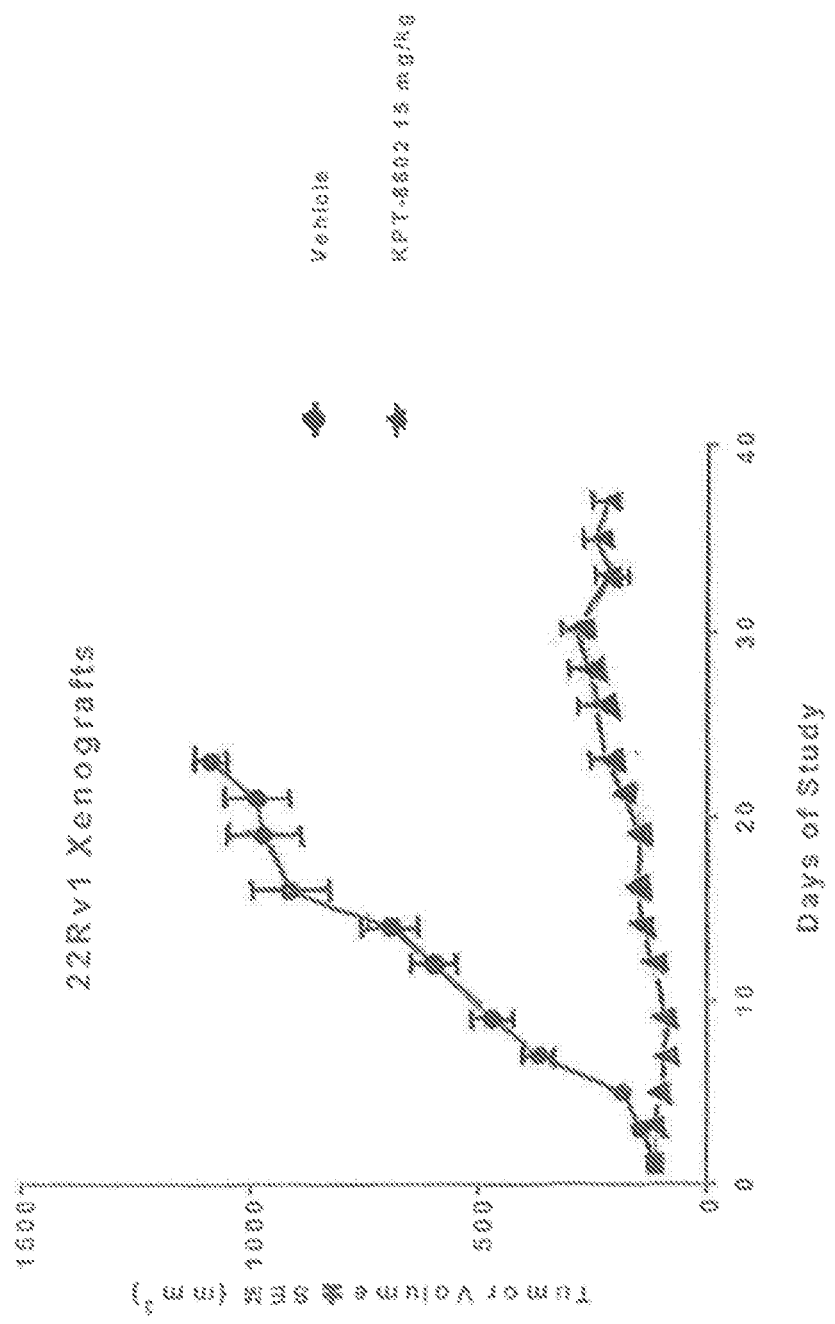
FIG. 3 is graph of tumor volume versus days post administration of KPT-8602 to mice subjected to a xenograft of 22Rv1 prostate cancer cells.
Figure 4:
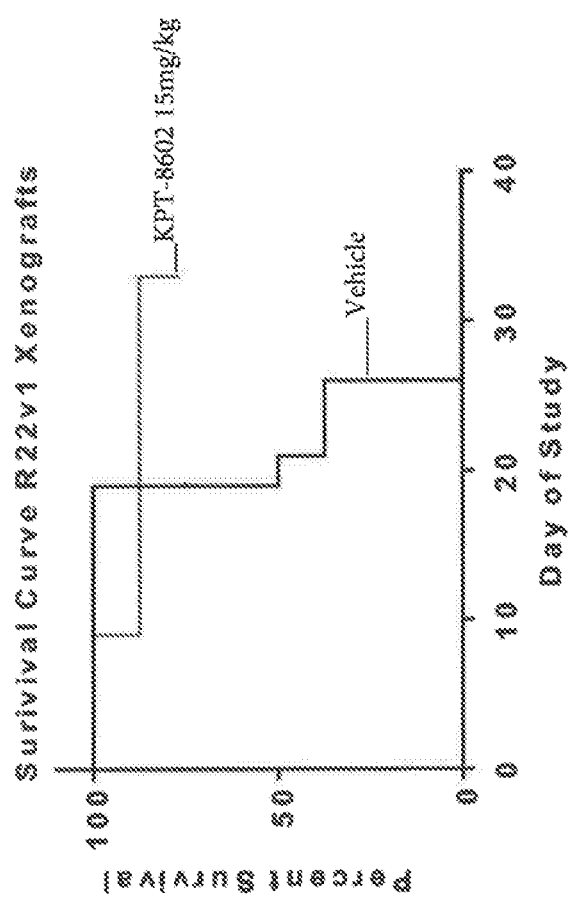
FIG. 4 is a graph of percent survival versus day post administration of KPT-8602 in mice subjected to a xenograft of 22Rv1 prostate cancer cells.

The effect of KPT-8602 (15 mg/kg, QDx5/week) in a 22Rv1 prostate cancer xenograft model in CB.17 SCID mice was evaluated. Mouse weights and tumor size were monitored three times a week. Each mouse was euthanized at the end of study (Day 35) or when tumor volume reached 1000 mm$^3$, whichever comes first. Tumors were collected and fixed in 10% formalin for histopathology analysis. % TGI (tumor growth inhibition) on Day 16 was 87% for the KPT-8602-treated animals, when compared to the vehicle (FIG. 3). Kaplan-Meier plot analysis showed that vehicle treated mice had a median OS (overall survival) of 20 days while KPT-8602 treated mice had an undefined median OS at end of the study (FIG. 4). These results show that KPT-8602 significantly inhibits tumor growth and prolongs survival.

Example 3: Treatment of 22Rv1 Prostate Cancer Xenograft with KPT-8602 in Combination with Abiraterone The effects of combination treatment with KPT-8602 and abiraterone was evaluated in the 22Rv1 prostate cancer xenograft model in ICR-SCID mice. Six days after 22Rv1 transplantation, mice were randomized into 4 groups: Untreated (n=5), abiraterone acetate treated (n=5), KPT-8602 treated (n=5) and combination treatment (n=6). Abiraterone (Selleckchem) was administered orally each day at a dose of 100 mg/kg for 3 weeks. KPT-8602 was administered orally at 20 mg/kg twice a week for a total of 7 doses. All mice were followed for measurement of subcutaneous tumors and observed for changes in body weight and any side effects. All tumors were collected at 24 hours after last dose of combination treatment and a tumor picture was taken.

Figure 5:
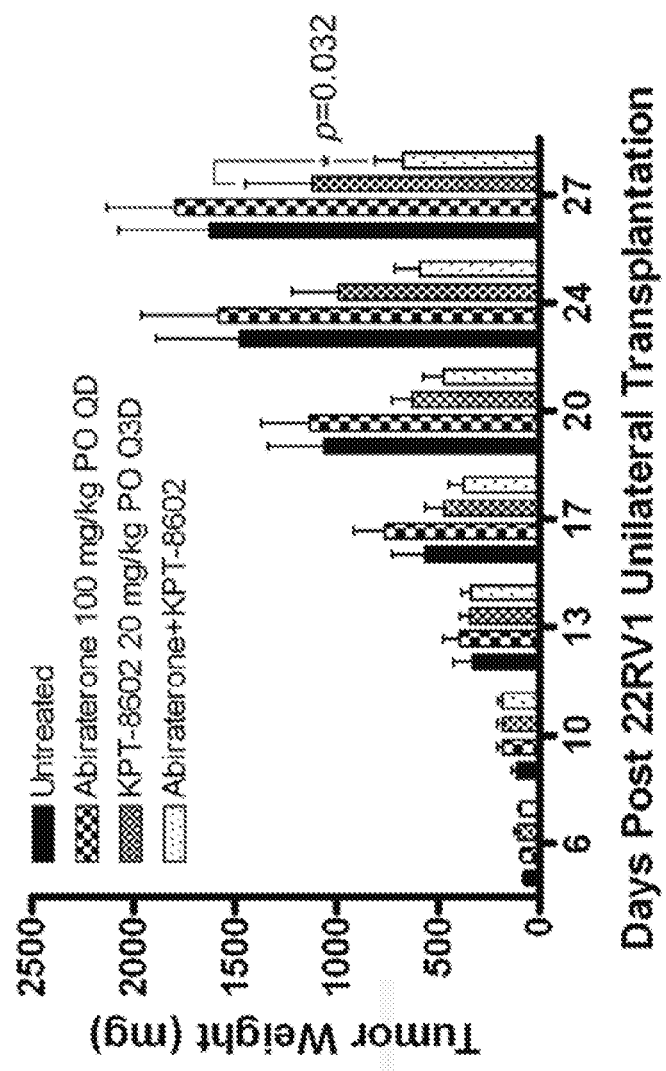
FIG. 5 is a graph of tumor weight versus days post administration of control, abiraterone, KPT-8602 and the combination of KPT-8602 and abiraterone in mice subjected to a xenograft of 22Rv1 prostate cancer cells.

FIG. 5 shows that treatment with the combination of KPT-8602 and abiraterone significantly inhibited the growth of tumors in mice as evidenced by decreased tumor weight.

Figure 6:
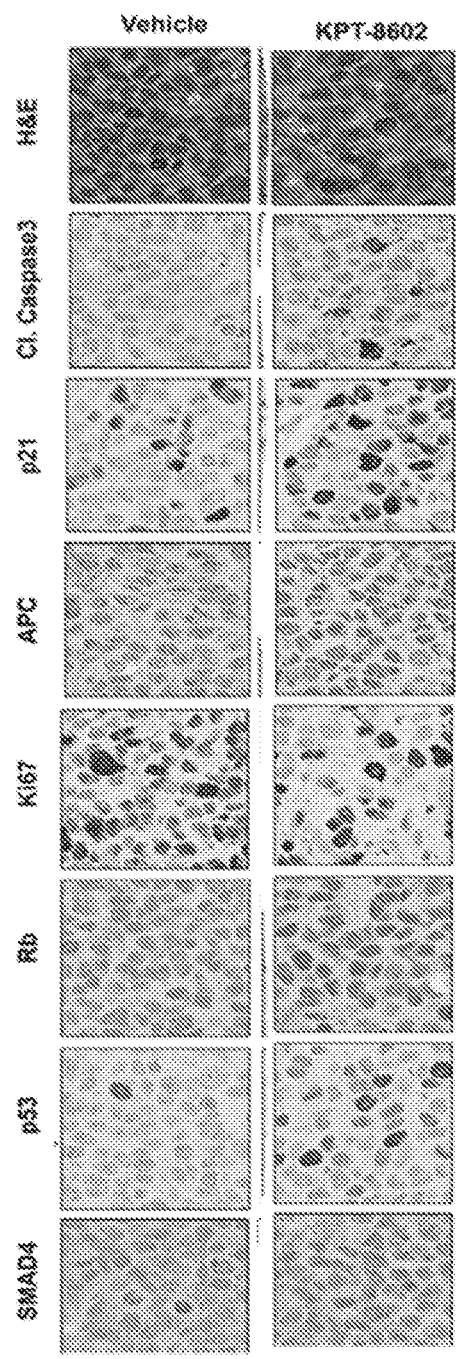
FIG. 6 shows immunohistochemistry analysis of xenograft samples derived from 22Rv1 cells treated with vehicle control or KPT-8602.

The immunohistochemistry analysis of xenograft samples derived from 22Rv1 cells treated with vehicle control or KPT-8602 showed decreased cell proliferation marker (Ki67) and increased apoptotic molecule (Cleaved Caspase 3) in KTP-8602-treated samples treated as compared to controls (FIG. 6). Increased nuclear staining of tumor suppressor proteins Rb, p21, p53, APC and SMAD4 were also observed in samples treated with KPT-8602.

Immunostaining

A tissue microarray (TMA) was constructed with tumor samples collected from 22Rv1 mouse prostate cancer cell.

Paraffin sections of the TMA were processed ans stained with antibodies using a Biogenex 16000 automated stainer. Digital images of the slides were obtained through an Aperio AT Turbo scanner 20×. The following antibodies were used for immunohistochemistry staining: Cleaved Caspase 3 (Cell Singaling Technology, 9661), p21 (Cell Signaling Technology, 2947), APC (Abcam, ab15270), Ki67 (Cell Marque, 275R-18), Rb (Abcam, ab181616, p53 (Santa Cruz, sc-126), and SMAD4 (Santa Cruz, sc-7966).

Example 4. Clinical Trial for Relapsed/Refractory Metastatic Castration Resistant Prostate Cancer (mCRPC)-Combination of KPT-8602 and Abiraterone Patients criteria selection: Patients currently receiving treatment with abiraterone and appropriate to continue in the opinion of the Investigator. Patients must also have been on and continue on a stable dose of corticosteroids (prednisone or dexamethasone) for 30 days prior to C1D1. Patients will continue to receive the dose and schedule of abiraterone and corticosteroids that they were receiving at the time of enrollment.

Other criteria include: histologically confirmed adenocarcinoma of the prostate; surgically or medically castrated with testosterone levels of <50 ng/dL (<2.0 nM); documented MCRPC progression as assessed by the Investigator with either Prostate specific antigen (PSA) progression defined by a minimum of 3 rising PSA levels with an interval of >1 week between each determination or radiographic progression of soft tissue disease by modified RECIST criteria 1.1 or of bone metastasis with 2 or more documented new bone lesions on a bone scan with or without PSA progression; zero to 2 previous taxane-based chemotherapy regimens; at least 2 weeks from completion of any radiotherapy; not transfusion dependent; albumin >2.5 g/dL; adequate hematopoietic function: ANC≥1000/mm$^3$, hemoglobin (Hb)≥9.0 g/dL, and platelet count≥100,000/mm$^3$; Eastern Cooperative Oncology Grop (ECOG) performance status≤1; and life expectancy≥4 months.

KPT-8602 with Abiraterone and Corticosteroids

Patients will be treated at a dose and schedule of KPT-8602 selected form Table 1 in combination with abiraterone and corticosteroids.

TABLE 1

KPT-8602 Dose Levels

| Cohort | KPT-8602 Dose Levels 28-Day Cycle |
|---|---|
| 1 | 5 mg |
| 2 | 10 mg |
| 3 | 20 mg |
| 4 | 30 mg |
| 5 | 40 mg |
| 6 | 60 mg |
| 7 | 80 mg |
| 8 | 100 |

Example 5. Clinical Trial Results for Relapsed/Refractory Metastatic Castration Resistant Prostate Cancer (mCRPC)-KPT-8602 Alone and in Combination with Abiraterone A. Patient Selection Criteria:

Relapsed/Refractory Metastatic Castration Resistant Prostate Cancer-All Treatment Groups (Monotherapy and Combination Therapy)

1. Histologically confirmed adenocarcinoma of the prostate with archival tumor tissue available for molecular analyses.

2. Surgically or medically castrated, with testosterone levels of <50 ng/dL (<2.0 nM).

3. Documented mCRPC progression as assessed by the Investigator with one of the following:
   a. Prostate specific antigen (PSA) progression defined by a minimum of 3 rising PSA levels (at approximately Day −30 and approximately Day −45) with an interval of >1 week between each determination. The PSA values at the Screening visit should be >2 μg/L (>2 ng/mL); patients on systemic glucocorticoids for control of symptoms must have documented PSA progression by Prostate Cancer Working Group 3 (PCWG3) while on systemic glucocorticoids prior to commencing C1D1 of treatment.
   b. Radiographic progression of soft tissue disease by modified RECIST criteria 1.1 or of bone metastasis with 2 or more documented new bone lesions on a bone scan with or without PSA progression.

4. Initial response (per modified PCWG3 Guidelines) to second generation anti-hormonal therapy (examples: abiraterone, enzalutamide, TAK 700), but later relapsed. Disease relapse would be defined as progressive disease at the time of entry per inclusion criterion 3.

5. Zero to 2 previous taxane-based chemotherapy regimens.

6. At least 2 weeks from completion of any radiotherapy including a single fraction of radiotherapy for the purposes of palliation (confined to one field) is permitted.

7. Patients should not be transfusion dependent.

8. Albumin>2.5 g/dL.

9. Adequate hematopoietic function: ANC≥1000/mm$^3$, hemoglobin (Hb)≥9.0 g/dL, and platelet count≥100,000/mm$^3$.

10. Eastern Cooperative Oncology Group (ECOG) performance status of ≤1.

11. Life expectancy of ≥4 months.

Additional Criteria for Combination Therapy Patients (KPT-8602 and Abiraterone)

12. Patients currently receiving treatment with abiraterone and appropriate to continue in the opinion of the Investigator (some patients may be progressing). Patients must also have been on and continue on a stable dose of corticosteroids (prednisone or dexamethasone) for 30 days prior to C1D1.

B. Patient Characteristics and Demographics

| Patient Characteristics | Single Agent QDx5 (N = 13) | +Abi QDx5 (N = 17) | All N = 30 |
|---|---|---|---|
| Median Age (range) | 72 (56-86) | 70 (48-84) | 71 (48-86) |
| Median Prior Treatments (range) | 5 (1-12) | 3 (1-8) | 4 (1-12) |

C. Dosing

Patients treated with KPT-8602 alone received oral KPT-8602 for 5 days per week (QDx5) at dose levels of 20 and 30 mg. Patients treated with KPT-8602 and abiraterone received oral KPT-8602 for 5 days per week (QDx5) at dose levels of 20 and 30 mg and the dose and schedule of abiraterone and corticosteroids that they were receiving at the time of enrollment. For example, a typical dose of ZYTIGA (abiraterone acetate) is 1000 mg orally once daily with prednisone 5 mg orally twice daily. A full cycle was 28 days long. A representative cycle of KPT-8602 dosing is oral administration 5 out of 7 consecutive days in a week for a 28-day cycle (e.g., Days 1-5, 8-12, 15-19 and 22-26 of each 28-day cycle).

D. Summary of Responses and Progression Free Survival (PFS)

| Cohort | N | PR | SD ≥8 weeks | SD ≥16 weeks | PD | DCR (PR + SD) SD ≥ 8 weeks | SD ≥ 16 weeks |
|---|---|---|---|---|---|---|---|
| Single Agent (KPT-8602) | 11 | 1 (9%) | 8 (72%) | 5 (45%) | 2 (18%) | 9 (82%) | 6 (55%) |
| KPT-8602 + Abiraterone and corticosteroid | 12 | 1 (8%) | 9 (75%) | 6 (50%) | 2 (17%) | 10 (83%) | 7 (58%) |
| Total | 23 | 2 (9%) | 17 (74%) | 11 (48%) | 4 (17%) | 19 (83%) | 13 (57%) |

Responses were assessed using RECIST v 1.1 criteria once every 28-day cycle. PR: Partial Response, SD: Stable Disease, PD: Progressive Disease, DCR: Disease Control Rate. 7 Non-evaluable patients: 2AE, 2 patient decision, 2 physician decision, 1 patient non-compliant.

Figure 7:
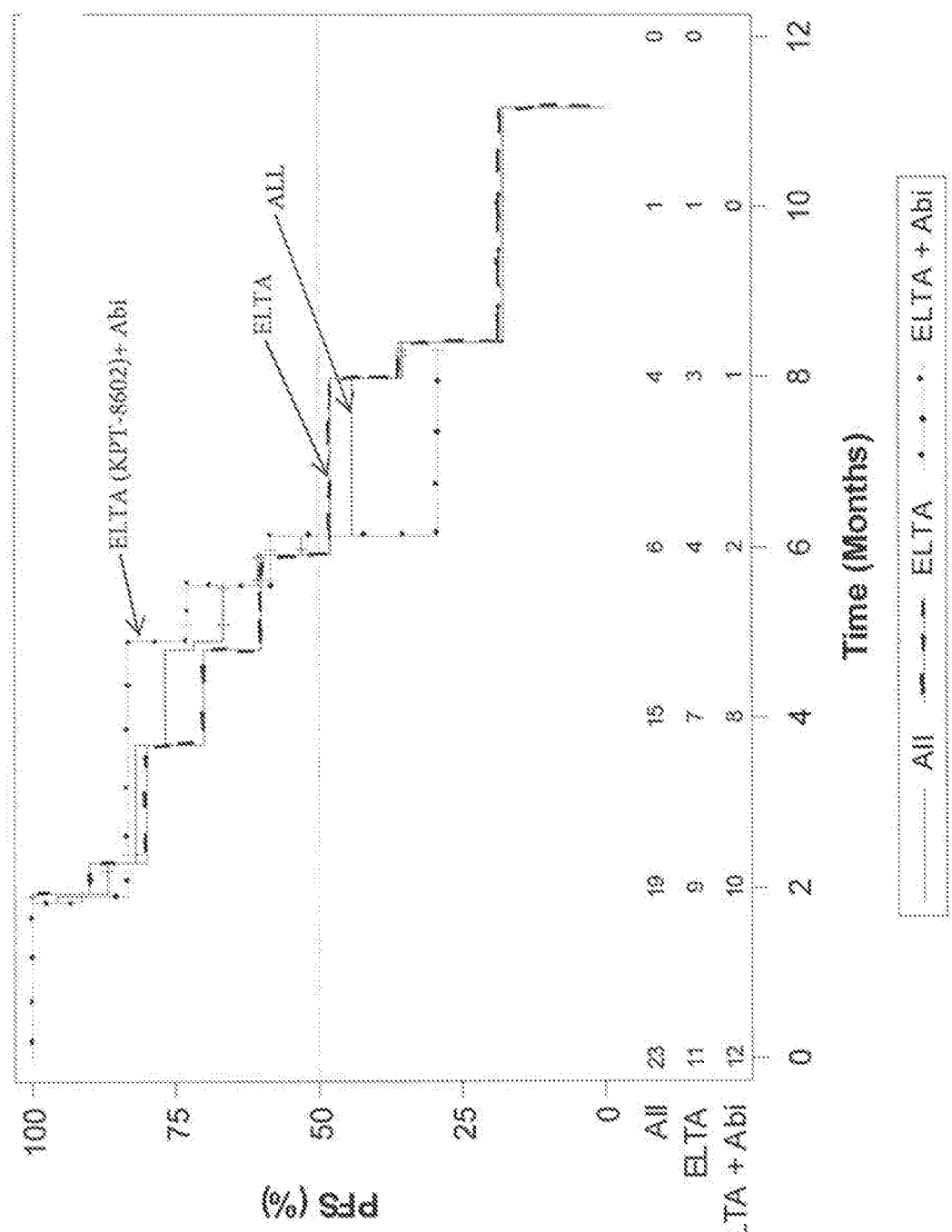
FIG. 7 is a plot of % Progression Free Survival (PFS) versus time in months for patients treated with KPT-8602 alone and in combination with abiraterone.

Using Kaplan-Meier analysis, the median PFS was 6.1 months (95% CI: 4.8, 8.4) among the 23 evaluable patients. Among evaluable patients treated with KPT-8602 alone, median PFS was 5.9 months (95% CI: 1.9, 11.2). Among 12 patients treated with KPT-8602 and abiraterone, median PFS was 6.1 months (95% CI: 1.9, NE). A plot of % PFS vs. Time (Months) is shown in FIG. 7.

All patients had their disease assessed per modified PCWG3 Guidelines including RECIST v1.1 (see below) by the following tests at pre-determined the time points.

PSA: Disease specific clinical lab assessment
Testosterone: Disease specific clinical lab assessment
Bone scan and CT (or MRI) scan of the abdomen and pelvis (RECIST v.1.1): Patients will receive a bone scan to monitor and assess bone disease progression and CT (or MRI) of the abdomen and pelvis (and chest, if indicated) to monitor and assess soft tissue disease progression per PCWG3 including RECIST v.1.1. Evaluation of soft tissue lesion by physical exams will also be conducted per RECIST v.1.1.
Radiographic disease progression is defined as PD by RECIST 1.1 for soft tissue disease or by the appearance of two or more new lesions on bone scan for bone disease (per modified PCWG3 guidelines).
Bone scan and CT/MRI of abdomen and pelvis (and chest if clinically indicated): Bone scan—Screening, C3D1, C5D1, Day 1 of every 3 cycles for cycles≥Cycle 7; and at the EoT Visit; CT/MRI—Screening, C3D1, C5D1, Day 1 of every 3 cycles for cycles≥Cycle 7; and at the EoT Visit.

Prostate Cancer Response Assessments

| Assessment | Target | Response Criteria | Response Definitions |
|---|---|---|---|
| PSA blood level | PSA | Modified PCWG3[1] | Favorable response: ≥30% decrease in PSA blood level within 3 months of baseline. SD: Neither favorable or unfavorable. Unfavorable response: ≥25% increase and ≥ 2 ng/mL increase from baseline beyond 12 weeks. |
| Bone Scan | Bone Lesions | Modified PCWG3[1] | CR: Disappearance of all bone lesions SD: Non-CR/Non-PD PD: 2 or more new lesions |
| CT Scan | Soft Tissue Lesions | RECIST v1.1[2] | CR: Disappearance of all target lesions PR: At least a 30% decrease in the sum of diameters of target lesions, taking as reference the baseline sum diameters SD: Steady state of disease. Non-CR/Non-PR/Non-PD PD: ≥20% increase in the sum of diameters of measured lesions taking as references the smallest sum of diameters recorded since the treatment started. In addition to the relative increase of 20%, the sum must also demonstrate an absolute increase of ≥5 mm. |

Abbreviations:
AR = androgen receptor;
CR = complete response;
mRNA = messenger ribonucleic acid;
PCWG3 = Prostate Cancer Working Group 3;
PD = progressive disease;
PR = partial response;
PSA = prostate specific antigen;
RECIST = Response Evaluation Criteria in Solid Tumors;
SD = stable disease
[1]Scher, HI., et al., 2016. Trial Design and Objectives for Castration-Resistant Prostate Cancer: Updated Recommendations From the Prostate Cancer Clinical Trials Working Group 3. J Clin Oncol 34, 1402-1418.
[2]Eisenhauer, E.A., et al. 2009. New response evaluation criteria in solid tumours: revised RECIST guideline (version 1.1). European journal of cancer 45, 228-247.

E. Time on Treatment (ToT)

The time on study in days for evaluable patients is shown in FIG. 8 and in the table below.

| | |
|---|---|
| Median ToT-all evaluable patients | 145 (40-368) |
| Median ToT-KPT-8602 alone-all doses (20 and 30 mg) | 96 |
| Median ToT-20 mg KPT-8602 | 96 |
| Median ToT-30 mg KPT-8602 | 134 |
| Median ToT with KPT-8602 + Abiraterone-all doses (20 and 30 mg KPT-8602) | 155 |
| Median ToT with 20 mg KPT-8602 + Abiraterone | 164 |
| Median ToT with 30 mg KPT-8602 + Abiraterone | 145 |

Patients remained on treatment longer in the KPT-8602+ Abiraterone (median: 155 days) compared to KPT-8602 alone (96 days).

What is claimed is:

1. A method of treating prostate cancer in an abiraterone-refractory subject in need thereof, comprising the combination administration to the subject over a 28-day treatment cycle of a first amount of abiraterone, and a second amount of a compound of Formula (I):

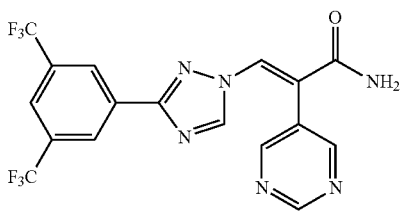

or a pharmaceutically acceptable salt thereof, wherein the first and second amounts together comprise an effective amount; and wherein the compound of Formula (I) is administered on days 1-5, 8-12, 15-19, and 22-26 of the 28-day treatment cycle and abiraterone is administered daily during the 28-day treatment cycle.

2. The method of claim 1, wherein the subject was previously administered at least one treatment regimen for prostate cancer, and further wherein, for each subject who previously received two or more treatment regimens, different active ingredients were administered in each treatment regimen.

3. The method of claim 1, wherein the compound of Formula (I) is administered at a dose of 5 mg to 40 mg per day.

4. The method of claim 1, wherein the prostate cancer is metastatic castration-resistant prostate cancer or castration-resistant prostate cancer.

5. The method of claim 1, wherein abiraterone is abiraterone acetate.

6. The method of claim 1, wherein abiraterone is administered orally once daily at a dose of 200 mg to 2000 mg.

7. The method of claim 1, wherein prednisone is administered in combination with abiraterone.

8. The method of claim 7, wherein prednisone is administered orally at a dose of 1 mg to 20 mg.

* * * * *